US00RE39152E

(19) United States
(12) Reissued Patent
Aust et al.

(10) Patent Number: US RE39,152 E
(45) Date of Reissued Patent: Jun. 27, 2006

(54) SURGICAL INSTRUMENT

(75) Inventors: Gilbert M. Aust, Huntsville, AL (US); Timothy E. Taylor, Huntsville, AL (US)

(73) Assignee: Endius Incorporated, Plainville, MA (US)

(21) Appl. No.: 09/707,445

(22) Filed: Nov. 6, 2000

Related U.S. Patent Documents

Reissue of:
(64) Patent No.: 5,540,706
Issued: Jul. 30, 1996
Appl. No.: 08/008,670
Filed: Jan. 25, 1993

(51) Int. Cl.
*A61B 17/32* (2006.01)

(52) U.S. Cl. ..... 606/170; 606/180; 604/22
(58) Field of Classification Search ..... 606/170, 606/180, 171; 604/95.04, 528, 22
See application file for complete search history.

(56) References Cited

U.S. PATENT DOCUMENTS

| | | | | |
|---|---|---|---|---|
| 3,470,876 A | | 10/1969 | Barchilon | |
| 3,605,725 A | | 9/1971 | Bentov | |
| 4,274,414 A | | 6/1981 | Johnson et al. | |
| 4,362,160 A | | 12/1982 | Hiltebrandt | |
| 4,499,899 A | * | 2/1985 | Lyons, III | |
| 4,517,977 A | * | 5/1985 | Frost | |
| 4,649,919 A | * | 3/1987 | Thimsen et al. | |
| 4,763,669 A | * | 8/1988 | Jaeger | 606/174 |
| 4,834,069 A | * | 5/1989 | Umeda | 128/4 |
| 4,834,729 A | * | 5/1989 | Sjostrom | |
| 4,880,015 A | | 11/1989 | Nierman | |
| 5,025,804 A | * | 6/1991 | Kondo | |
| 5,100,426 A | * | 3/1992 | Nixon | 606/159 |
| 5,143,475 A | * | 9/1992 | Chikama | 403/220 |
| 5,178,129 A | * | 1/1993 | Chikama et al. | 128/4 |
| 5,209,747 A | | 5/1993 | Knoepfler | |
| 5,285,795 A | * | 2/1994 | Ryan et al. | 128/750 |
| 5,295,990 A | | 3/1994 | Levin | |
| 5,330,502 A | | 7/1994 | Hassler et al. | |
| 5,354,311 A | * | 10/1994 | Kambin et al. | 128/751 |

FOREIGN PATENT DOCUMENTS

| | | |
|---|---|---|
| DE | 3920706 A1 | 1/1991 |
| DE | 4136861 A1 | 5/1993 |
| DE | 4204051 A1 | 8/1993 |
| EP | 0301288 A1 | 2/1989 |
| FR | 2662778 | 12/1991 |
| WO | 9300048 | 1/1993 |
| WO | 9304634 | 3/1993 |
| WO | 9320760 | 10/1993 |
| WO | 9320768 | 10/1993 |

* cited by examiner

*Primary Examiner*—Michael H. Thaler
(74) *Attorney, Agent, or Firm*—Tarolli, Sundheim, Covell & Tummino L.L.P.

(57) ABSTRACT

A surgical instrument includes a tubular stem section which extends from a handle. A tubular articulated section connects a surgical instrument with the stem section. An actuator assembly is connected with the handle and is operable to bend the articulated section to change the orientation of an instrument on an outer end portion of the articulated section relative to body tissue. The instrument on the outer end of the articulated section may be a rotatable cutting tool which is driven by a tubular drive element having a flexible section which extends through the articulated section. The articulated section is bent or flexed by a plurality of flexible elongated elements (wires). In one embodiment of the invention, a pair of elongated elements are provided to flex the articulated section in opposite directions. In another embodiment of the invention, four flexible elongated elements are provided to flex the articulated section in any one of four directions.

9 Claims, 5 Drawing Sheets

SURGICAL INSTRUMENT

Matter enclosed in heavy brackets [ ] appears in the original patent but forms no part of this reissue specification; matter printed in italics indicates the additions made by reissue.

BACKGROUND OF THE INVENTION

The present invention relates to a new and improved arthroscopic/endoscopic surgical instrument, and more specifically, to an arthroscopic/endoscopic surgical instrument which may be used to remove tissue from a joint or other body space.

Surgical instruments which may be used to remove tissue or perform other operations on tissue are disclosed in U.S. Pat. Nos. 4,499,899; 4,517,977; 4,649,919; and 4,834,729. The surgical instruments disclosed in these patents have stem sections which extend outwardly from a handle. A cutting tool or other device is disposed at the outer end of the stem section. The stem section is rigid. Therefore, the orientation of the cutting tool can not be changed relative to the stem section.

SUMMARY OF THE INVENTION

The present invention relates to a surgical instrument which is particularly well adapted for arthroscopic and/or endoscopic surgery. The surgical instrument has a stem section which is attached to a handle. A suitable instrument, such as a cutting tool, is connected with an outer end portion of the stem section by an articulated section. An actuator is provided to bend the articulated section to change the orientation of the instrument relative to the stem section and body tissue.

In one embodiment of the invention, a pair of flexible elongated elements, such as wires, are provided to bend the articulated section in opposite directions from an initial position. In this embodiment of the invention, the articulated section may be constructed so as to freely flex in a direction transverse to the direction in which the articulated section is bent by the elongated elements. In another embodiment of the invention, a plurality of elongated elements, such as wires, are provided to flex or bend the articulated section in any one of four directions.

BRIEF DESCRIPTION OF THE DRAWINGS

The foregoing and other objects and features of the present invention will became room apparent upon a consideration of the following description taken in connection with the accompanying drawings, wherein.

DESCRIPTION OF SPECIFIC PREFERRED EMBODIMENTS OF THE INVENTION

General Description

Figures 1, 2:
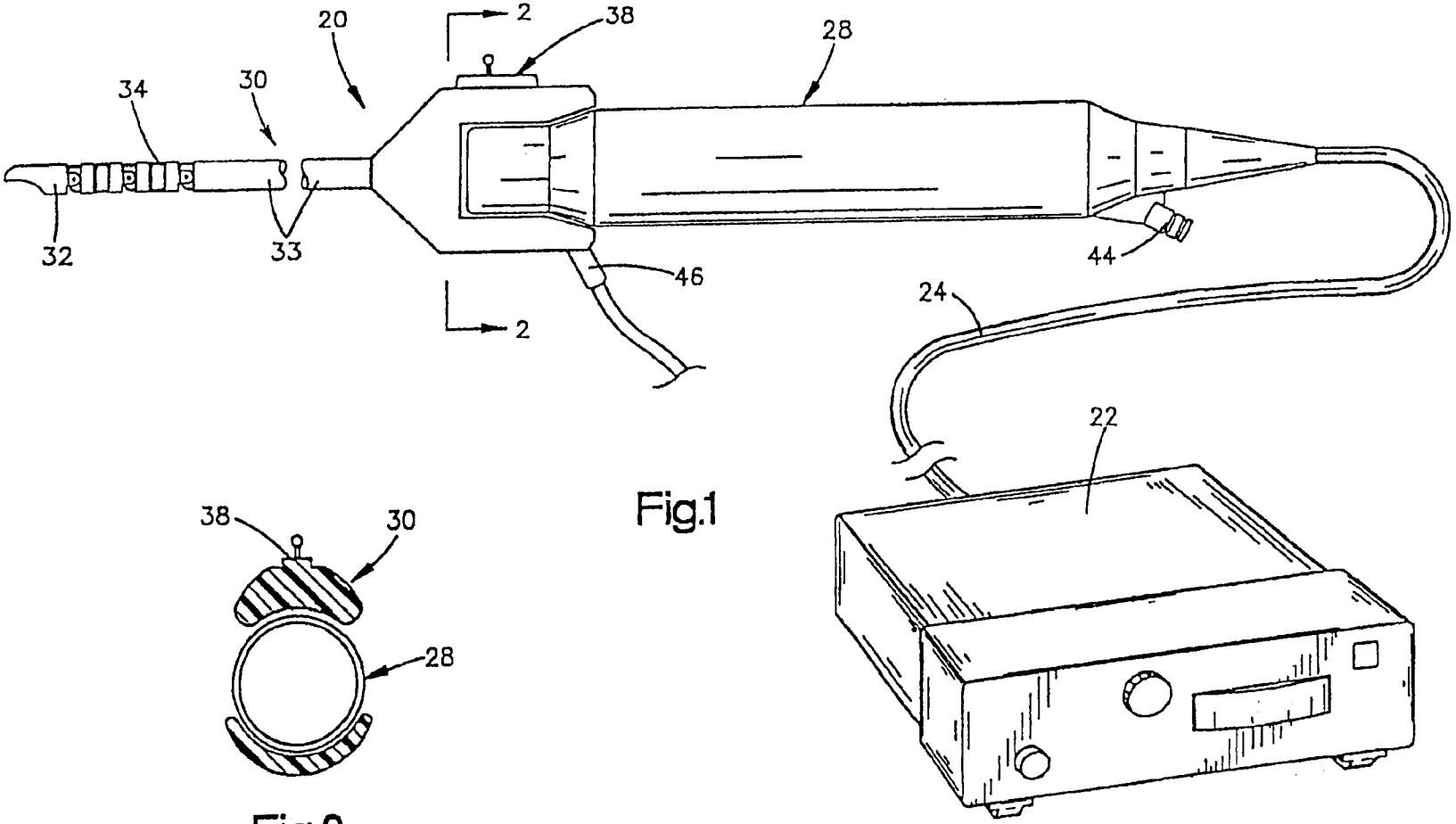
FIG. 1 is a schematic illustration of a surgical instrument constructed in accordance with the present invention.
FIG. 2 is a schematic sectional view, taken generally along the line 2—2 of FIG. 1, illustrating the manner in which a known handle is connected with a tubular stem section of the surgical instrument.

A surgical instrument 20, constructed in accordance with the present invention, is illustrated in FIG. 1 and may be used during the performance of arthroscopic and/or endoscopic surgery. A control apparatus 22 is connected with the surgical instrument 20 through a cord system 24. The surgical instrument 20 includes a handle 28 of known construction, which is connected with a tubular stem section 30. A known instrument 32 is connected with a rigid portion 33 of the stem section by an articulated section 34 constructed in accordance with the present invention.

In accordance with one of the features of the present invention, an actuator assembly 38 is manually operable to bend the articulated section 34 to move the instrument 32 between my one of many positions relative to the rigid portion 33 of the stem section 30. The actuator assembly 38 can be operated to bend the articulated section 34 from a straight or initial condition shown in FIGS. 4 and 5 to any one of a plurality of bent conditions, some of which have been indicated schematically in FIG. 7. Thus, the actuator assembly 38 can be operated to bend the articulated section 34 upwardly from the straight or initial orientation (shown in solid lines in FIGS. 4, 5 and 7) through a plurality of positions, indicated in dashed lines aid dash-dot lines to a fully flexed position indicated in dash-dot-dot lines in FIG. 7.

Figure 7:
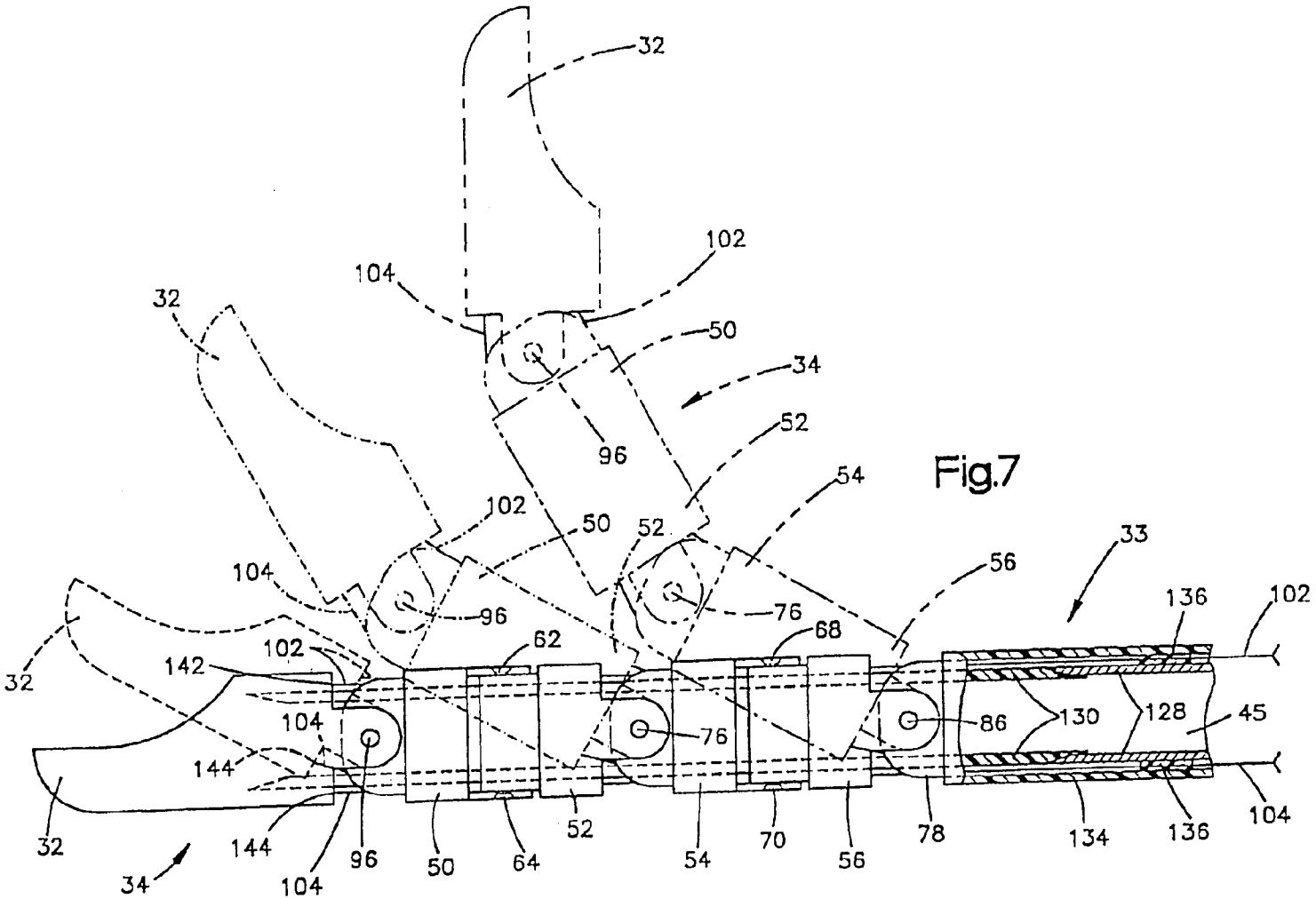
FIG. 7 is an enlarged schematic side elevational view, generally similar to FIG. 4, illustrating the manner in which the articulated section is flexed by the actuator assembly of FIG. 6.

Of course, operation of the actuator assembly 38 could be interrupted with the instrument 32 in any one of the positions illustrated in FIG. 7 or in positions intermediate the positions shown in FIG. 7. In addition, the actuator assembly 38 can be operated to deflect the articulated section 34 downwardly (as viewed in FIGS. 4 and 7) to any one of a plurality of positions. When the actuator assembly 38 has been operated to bend the articulated section 34 downward to a fully deflected position, the instrument 32 will extend straight downwardly in much the same manner as in which the instrument has been shown extending straight upwardly in dash-dot-dot lines in FIG. 7 Thus, the actuator assembly 38 is operable to bend the articulated section 34 and to move the instrument 32 relative to the rigid portion 33 of the stem section 30 in such a manner as to change the orientation of the instrument 32 through 90° to either a straight upward orientation (as shown in dash-dot-dot lines in FIG. 7) or to a straight downward orientation.

Figure 3:
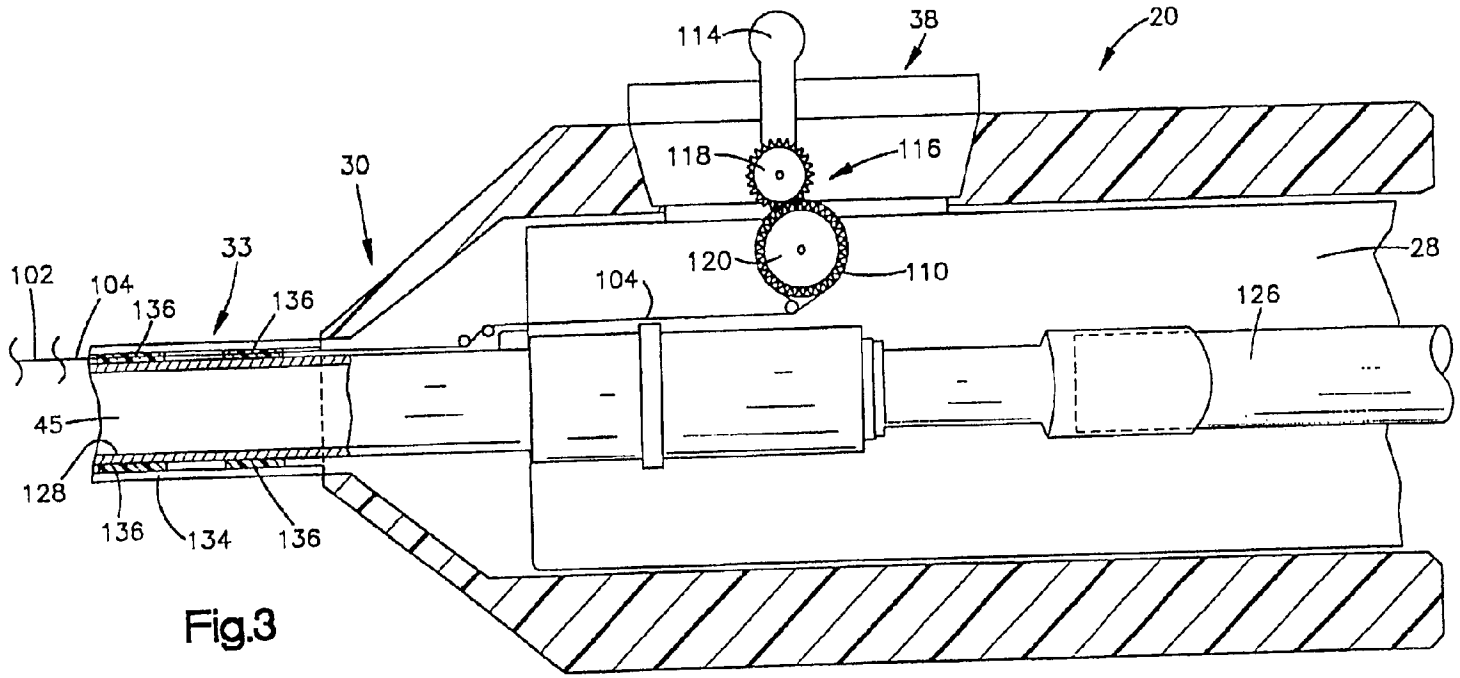
FIG. 3 is an enlarged schematic sectional view depicting the manner in which an actuator for bending an articulated section of the surgical instrument is mounted on the stem section and the manner in which a drive shaft is connected with a tubular drive element which extends through the stem section.
Figure 4:
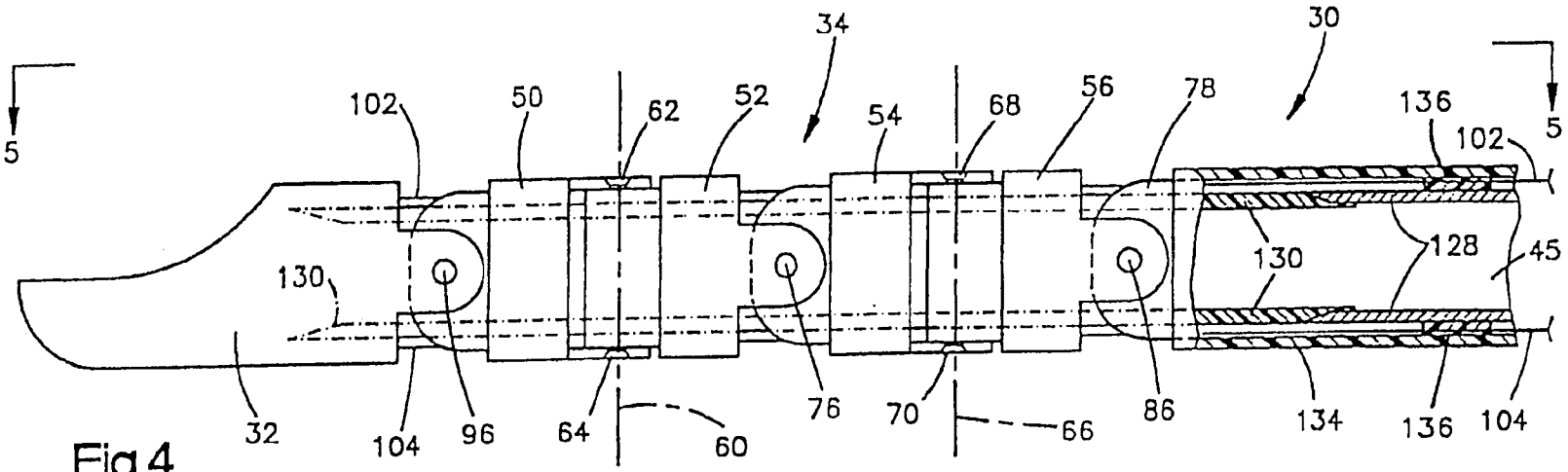
FIG. 4 is an enlarged schematic side elevational view depicting the construction of an articulated section of the stem section.
Figure 5:
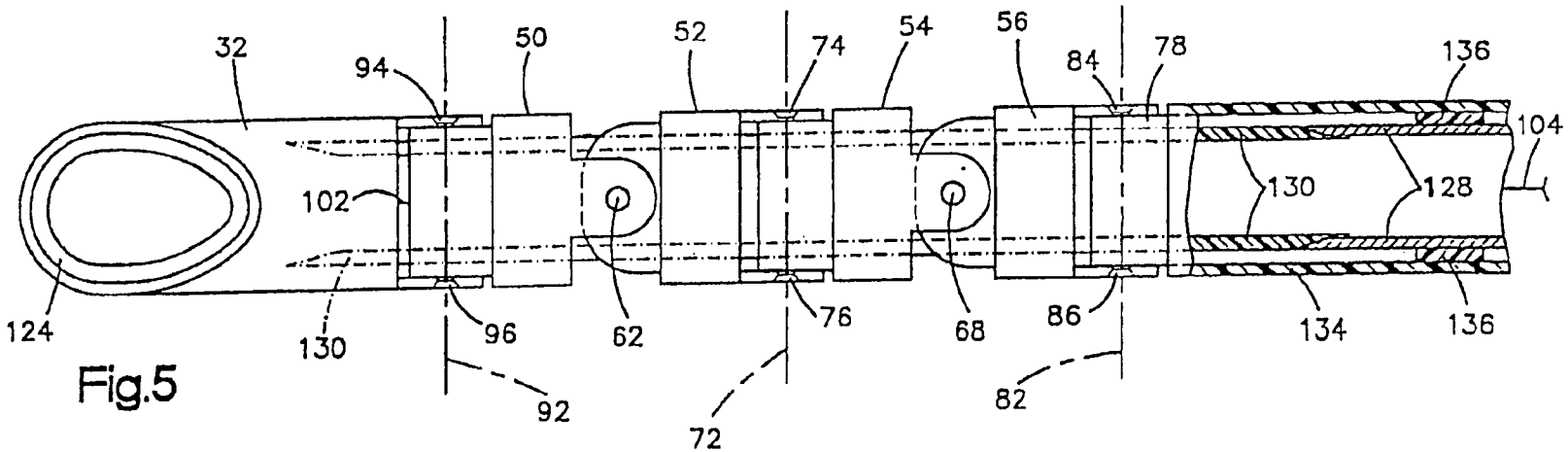
FIG. 5 is a schematic plan view, taken generally along the line 5—5 of FIG. 4, further illustrating the construction of the articulated section of the stem section.

In accordance with another feature of the embodiment of the invention illustrated in FIGS. 1–8, the articulated section 34 can be freely bent or deflected sidewardly, that is either up or down as viewed in FIG. 5 or into and out of the sheet as viewed in FIGS. 4 and 7. Although the actuator assembly 38 is operable to positively deflect or bend the articulated section either up or down as viewed in FIG. 4, the articulated section 34 is allowed to float or bend sidewardly under the influence of forces applied to the articulated section.

The actuator assembly 38 can be operated to change the orientation of the instrument 32 relative to the rigid portion 33 of the stem section 30 and body tissue during an operation. The actuator assembly 38 can be operated to positively change the orientation of the instrument 32 through a range of 180°, that is through 90° upwardly (as viewed in FIGS. 4 and 7) from the straight initial orientation and through 90° downwardly (as viewed in FIGS. 4 and 7) from the straight initial orientation. In addition, the articulated section 34 can be deflected or bent under the influence of forces applied to the instrument 32, through 90° to either side of the straight initial orientation shown in FIGS. 4 and 5.

It is believed that the surgical instrument 20 will be particularly advantageous for removing tissue from between vertebra in the human spinal column during an operation. Thus, the instrument 32, articulated section 34 and part of the rigid portion 33 of the stem section 30 can be inserted through a very small opening in the skin adjacent to the spinal column of a patient. As this is done, the articulated section 34 is straight in the initial orientation shown in FIGS. 1, 4 and 5.

After the stem section 30 has been partially inserted through an opening in the skin adjacent to the spinal column, the actuator assembly 38 is operated to bend the articulated section 34 and move the surgical instrument 32 transversely to a longitudinal central axis of the rigid portion 33 of the stem section 30. This enables the instrument 30 to be moved to a desired position to engage tissue located between adjacent vertebra. As the instrument 32 is being moved by operation of the actuator assembly 38, the articulated section 34 can also be deflected sideways under the influence of forces applied against the instrument 32. Of course, the surgical instrument 20 can be used during the performance of many different types of arthroscopic and/or endoscopic operations.

During use of the surgical instrument 20, it is contemplated that it will be desirable to convey tissue removed from between vertebra or other locations away from the instrument 32. Accordingly, a suction pump (not shown) is connected with the handle 28 at a connection 44. Suction is conducted through a central conduit or passage 45 (FIGS. 3 and 4) in the stem section 30 to the instrument 32. The suction draws or pulls tissue from the area immediately adjacent to the instrument 32 back through the stem section 30 to the connection 44 and suction conduit In addition, water or other fluid can be utilized to irrigate the area where tissue is removed by the instrument 32. Thus, a source of water or other irrigation fluid is connected with the handle 28 at a connection indicated at 46 in FIG. 1. The irrigation fluid is conducted through the handle 28 and the central conduit 45 in the stem section 30 to the instrument 32. Irrigating fluid, along with the removed tissue, is then withdrawn from the area around the surgical instrument 32.

Articulated Section

The articulated section 34 includes a plurality of relatively movable sections 50, 52, 54 and 56 (FIGS. 4 and 5). The sections 50, 52, 54 and 56 are interconnected for pivotal movement about perpendicular axes. Thus, the section 50 is pivotal relative to the section 52 about a vertical axis indicated at 60 in FIG. 4. The section 50 is connected with the section 52 at pivot connections 62 and 64. Similarly, the section 54 is pivotal relative to the section 56 about a vertical axis indicated at 66 in FIG. 4. The section 54 is connected with the section 56 at pivot connections 68 and 70.

The section 52 is pivotal relative to the section 54 about a horizontal axis indicated at 72 in FIG. 5. The section 52 is connected with the section 54 at pivot connections 74 and 76. Similarly, the section 56 is pivotal relative to an end portion 78 of the rigid stem section 33 about a horizontal axis indicated at 82 in FIG. 5. The section 56 is connected with the rigid portion 33 of the stem section 30 at pivot connections 84 and 86.

The instrument 32 is pivotal relative to the section 50 about a horizontal axis indicated at 92 in FIG. 5. The instrument 32 is connected with the section 50 at pivot connections 94 and 96.

The axes 60 and 66 (FIG. 4) extend parallel to each other and perpendicular to a longitudinal central axis of the stem section 30. Similarly, the axes 72,82 and 92 (FIG. 5) extend parallel to each other and perpendicular to a longitudinal central axis of the stem section 30. The axes 60 and 66 extend perpendicular to the axes 72, 82 and 92. The axes 60, 66, 72, 82 and 92 all intersect the central axis of the stem section 30.

Initial operation of the actuator assembly 38 in one direction pivots the instrument 32 upwardly (as shown in FIG. 7) from the initial position shown in solid lines to the deflected position shown in dashed lines. Movement of the instrument 32 from the initial position shown in solid lines to the deflected position shown in dashed lines, is accomplished by pivotal movement of the instrument about the axis 92 at the pivot connections 94 and 96 (FIG. 5).

Continued operation of the actuator assembly 38 pivots the sections 50 and 52 together while the instrument 32 is maintained in a deflected position. Thus, the sections 50 and 52 pivot upwardly from the initial position shown in solid lines in FIG. 7 to the position shown in dash-dot lines in FIG. 7. As this occurs, the sections 50 and 52 pivot about the axis 72 (FIG. 5) at the pivot connections 74 and 76. During this movement, the orientation of the instrument 32 relative to the section 50 remains constant Continued operation of the actuator assembly 38 pivots the sections 54 and 56 upwardly (as viewed in FIG. 7) from the initial position shown in solid lines to the position shown in dash-dot-dot lines. The instrument 32 and sections 50 and 52 are maintained in the same orientation relative to each other during this pivotal movement of the sections 54 and 56. Thus, continued operation of the actuator assembly 38 pivots the sections 54 and 56 about the axis 82 (FIG. 5) at the pivot connections 84 and 86.

During deflection of the articulated section 34 about the axes 72, 82 and 92 (FIG. 5) by operation of the actuator assembly 38, the articulated section 34 is also free to deflect sideways under the influence of forces applied against the articulated section. Thus, the section 50 and the instrument 32 are pivotal sideways relative to the section 52 about the axis indicated at 60 in FIG. 4. The section 50 is pivotal sideways at the connections 62 and 64. The sections 50, 52 and 54 are pivotal sideways relative to the section 56 about the axis indicated at 66 in FIG. 4. The section 54 is pivotal sideways at the connections 68 and 70.

Actuator Assembly

The actuator assembly 38 includes a pair of flexible wires 102 and 104 (FIGS. 6 and 7) which are connected with the instrument 32 through the tubular stem section 30. The wire 102 is connected with the upper (as viewed in FIG. 7) portion of the instrument 32 while the wire 104 is connected with the lower portion of the instrument 32. The wires 102 and 104 are offset from the pivot connections 94 and 96 (FIGS. 5 and 7).

Tension in the upper wire 102 (as viewed in FIG. 7) is effective to pivot the instrument 32 in a clockwise direction about the pivot connections 94 and 96. Similarly, tension in the lower wire 104 is effective to pivot the instrument 32 in a counterclockwise direction (as viewed in FIG. 7) about the pivot connections 94 and 96.

When the actuator assembly 38 (FIG. 6) is operated in one direction, the wire 102 shortens slightly and the wire 104 is lengthened to pull the instrument 32 from the initial position shown in solid lines to the position shown in dashed lines in FIG. 7. Once the instrument 32 reaches the position shown in dashed lines in FIG. 7, further shortening of the wire 102 and lengthening of the wire 104 by operation of the actuator assembly 38 pulls the sections 50 and 52 in a clockwise direction (as viewed in FIG. 7) from the initial position shown in solid lines to the position shown in dash-dot lines in FIG. 7. As this occurs, the section 52 pivots about the axis 72 at the connections 74 and 76.

Continued operation of the actuator assembly 38 continues to shorten the wire 102 and lengthen the wire 104. This results in the sections 54 and 56 being pulled in a clockwise direction (as viewed in FIG. 7) from the initial position shown in solid lines to the position shown in dash-dot-dot lines. As this occurs, the sections 54 and 56 pivot about the axis 82 (FIG. 5) at the connections 84 and 86.

Operation of the actuator assembly 38 in the opposite direction is effective to shorten the wire 104 and lengthen the wire 102. As the actuator assembly is operated in the opposite direction to shorten the wire 104, the instrument 32 is pivoted downwardly or in a counterclockwise direction (as viewed in FIG. 7) about the axis 92 (FIG. 5) at the connections 94 and 96.

Continued operation of the actuator assembly 38 results in further lengthening of the wire 102 and shortening of the wire 104. This results in the sections 50 and 52 being pivoted downwardly or in a counterclockwise direction (as viewed in FIG. 7) about the axis 72 at the pivot connections 74 and 76. Still further operation of the actuator assembly 38 to lengthen the wire 102 and shorten the wire 104 results in the sections 54 and 56 pivoting downwardly a in a counterclockwise direction (as viewed in FIG. 7) about the axis 82 at the connections 84 and 86 (FIG. 5). Thus, the articulated sections 34 can be deflected or bent either upwardly, in the manner shown in FIG. 7, or downwardly depending upon the direction of operation of the actuator assembly 38.

Figure 6:
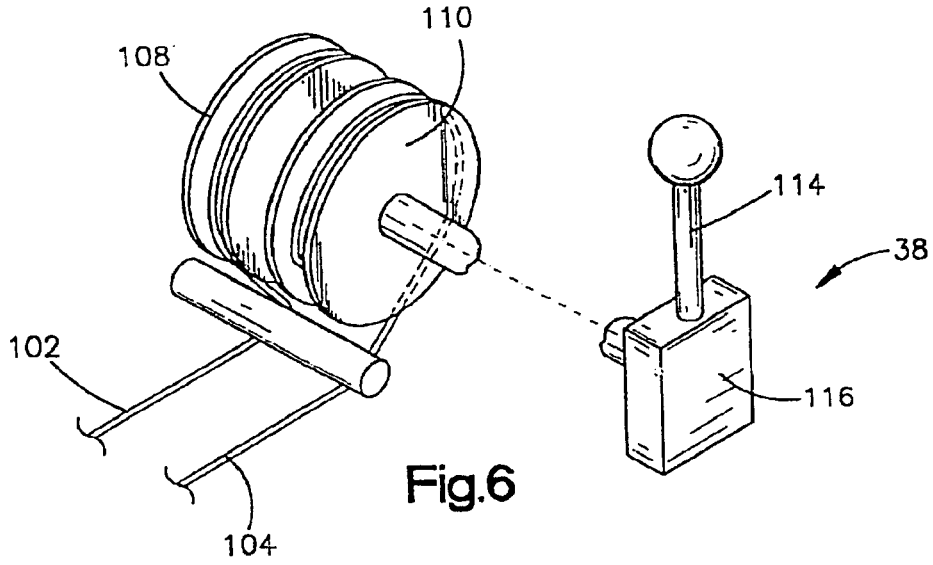
FIG. 6 is a highly schematicized illustration depicting the manner in which a pair of wires are connected with an actuator assembly which tensions one of the wires to bend the articulated section of the stem section.

The actuator assembly 38 has been shown schematically in FIG. 6. The actuator assembly 38 includes a pair of pulleys or drams 108 and 110 to which end portions of the wires 102 and 104 are connected The wires 102 and 104 are wound in opposite directions about the drums 108 and 110. The drums 108 and 110 rotate together about a common axis. Therefore, when one of the wires 102 or 104 is wound onto a drum 108 or 110, the other wire is unwound from the other drum.

Upon pivotal movement of a handle 114, a gear train 116 is actuated. The gear train 116 has been illustrated schematically in FIG. 3. The gear train 116 includes a gear 118 which is fixedly connected with the handle 114 and a gear 120 which is fixedly connected with the pulleys or drums 108 and 110 (FIG. 6).

Upon pivotal movement of the lever 114 toward the left or in a counterclockwise direction as viewed in FIG. 3, the gear 120 and drums 108 and 110 (FIG. 6) are rotated in a clockwise direction. Ibis results in the wire 102 being wound onto the drum 108 and the wire 104 being unwound from the drum 110. As was previously explained, shortening or winding up of the wire 102 results in the instrument 32 being pivoted upwardly or in a clockwise direction as viewed in FIG. 7.

Continued operation of the actuator assembly 38 results in continued shortening or winding up of the wire 102 and lengthening or unwinding of the wire 104 until the instrument 32 has been moved through 90° from the original orientation shown in solid lines in FIG. 7 to the deflected orientation shown in dash-dot-dot lines in FIG. 7. Since the wire 104 is wound around the drum 110 in the opposite direction from the direction in which the wire 102 is wound around the drum 108, the wire 104 is lengthened as the wire 102 is shortened.

Pivotal movement of the handle 114 in a clockwise direction (as viewed in FIG. 3) rotates the gear 120 and drums 1108 and 110 (FIG. 6) in a counterclockwise direction. This results in the wire 104 being wound onto the drum 110 as the wire 102 is wound off of the drum 108. Shortening of the wire 104 and corresponding lengthening of the wire 102 results in the articulated section 34 being pivoted downwardly or in a counterclockwise direction as viewed in FIG. 7 in the manner previously explained.

It should be understood that although one specific preferred embodiment of the actuator assembly 38 has been illustrated schematically and described herein, it is contemplated that the actuator assembly 38 could have a somewhat different construction if desired Thus, many different types of mechanisms could be provided lengthening one of the wires 102 or 104 while simultaneously shortening one of the wires.

Regardless of the type of actuator assembly 38 which is utilized to deflect or bend the articulated section 34, the actuator assembly is operable to apply force to the articulated section to deflect the articulated section from a straight initial configuration to an upwardly or downwardly (as viewed in FIG. 7) bent configuration. Thus, upon operation of the actuator assembly 38, the articulated section 34 can be deflected in the manner shown in dashed, dash-dot and dash-dot-dot lines in FIG. 7. This will result in the instrument 32 being moved upwardly from a position in which it is aligned with a horizontal Z axis (FIG. 8) to a position in which it is aligned with a vertical Y axis. The Z axis is coincident with a longitudinal central axis of the rigid portion 33 of the stem section 30.

Figure 8:
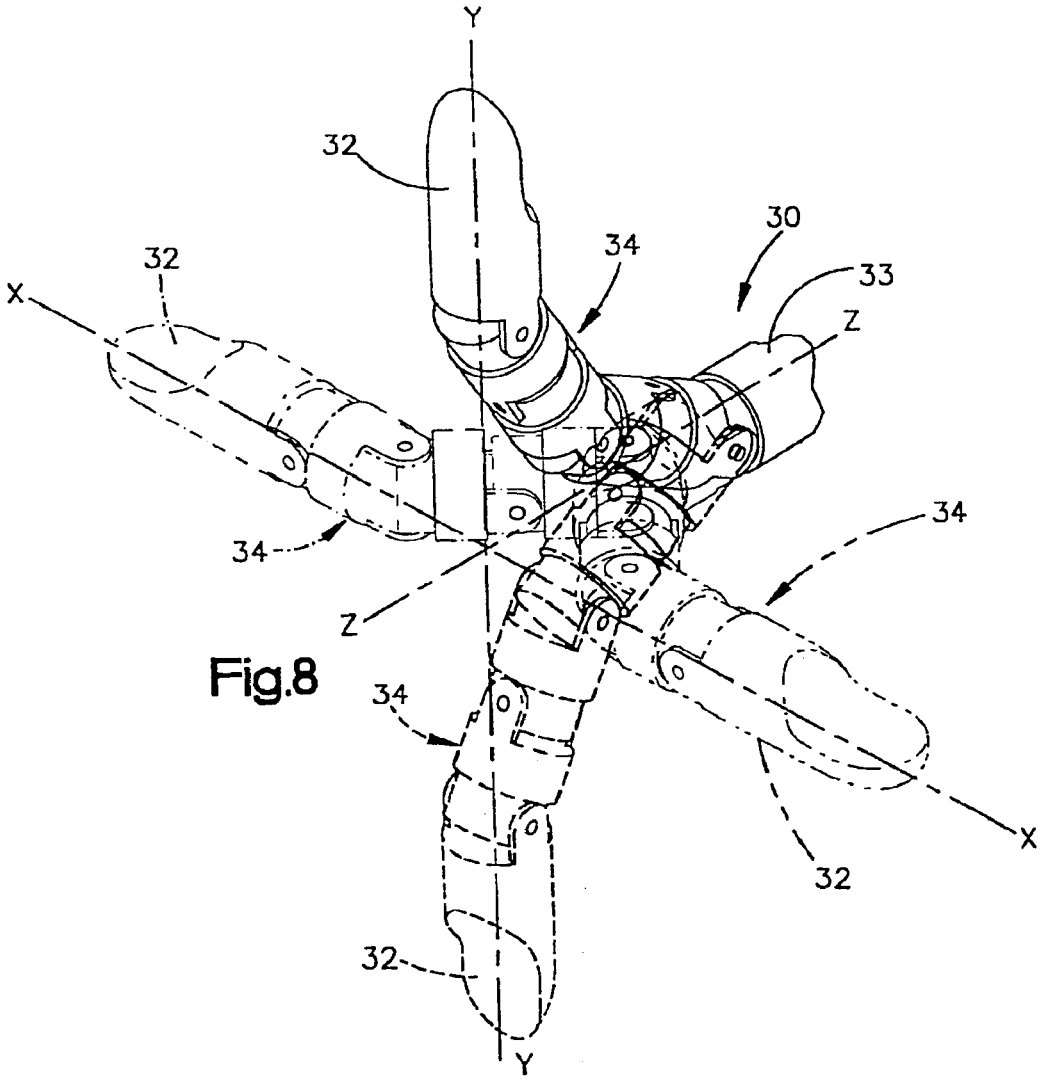
FIG. 8 (on sheet 4 of the drawings) is a highly schematicized illustration depicting deflection of the articulated section in either one of two directions by the actuator assembly of FIG. 6 and depicting the manner in which the articulated section is free to move in either one of two transverse directions.

The actuator assembly 38 can also be operated to bend or deflect the articulated section 34 to move the instrument 32 downwardly from the Z axis into alignment with the Y axis in the manner shown in dashed lines in FIG. 8. At this time, the instrument 32 extends downwardly from and perpendicular to the X and Z axes.

The actuator assembly 38 is operable to deflect the articulated section 34 to move the instrument 32 in either one of two directions, that is upwardly or downwardly as viewed in FIGS. 7 and 8. However, the articulated section 34 is deflectable to enable the instrument to be moved sidewardly. Thus, the articulated section 34 can be moved, under the influence of external or sidewards forces applied against the instrument 32, to move the instrument from the initial position toward the left into alignment with the X axis as shown in dash-dot lines in FIG. 8. Similarly, the instrument 32 can be deflected toward the right (as viewed in FIG. 8) into alignment with the X axis in the manner shown in dash-dot-dot lines. By a combination of operation of the actuator assembly 38 and sideward deflection of the instrument 32, the articulated section 34 can be deflected in such a manner as to move the instrument 32 into almost any position within a hemisphere having a central polar axis which is coincident with the Z axis (FIG. 8).

Instrument

In the embodiment of the invention illustrated in FIGS. 4 and 5, the instrument 32 includes a rotatable cutter 124 (FIG. 5). The cutter 124 is connected with a drive shaft 126 (FIG. 3) of a motor in the handle 28 (FIG. 1). During operation of the motor, the cutter 124 is rotated to cut tissue. Although the cutter 124 may have many different constructions, it is contemplated that the cutter my be constructed in a manner similar to that disclosed in U.S. Pat. No. 4,598,710.

Other known surgical instruments may be substituted for the cutter 124. Thus, a generally spherical rotatable burr or muter may be used to abrade tissue. If desired, a probe or a basket biter having (mown constructions could be substituted for the cutter 124. Of course, the particular type of instrument 32 which is connected with the outer end portion of the articulated section 34 will depend upon the surgical operation to be performed.

The cutter 124 is rotatable about the longitudinal central axis of the stem section 30 to cut tissue. A rigid tubular metal drive shaft 128 extends axially from the drive shaft 126 through the rigid portion 33 of the stem section 30 to the articulated section 34 (FIGS. 3, 4 and 5). Since the articulated section 34 is capable of being deflected in any desired direction, the rigid drive shaft 128 stops short of the articulated section 34 and is secured to a flexible tubular polymeric drive shaft 130 (FIG. 7). The flexible drive shaft 130 extends through the articulated section 34 and is connected to the rotatable cutter 24.

The rigid drive shaft 129 is connected with the drive shaft 126 (FIG. 3) of a suitable electric motor in the handle 28 and is rotated about its longitudinal central axis by operation of the motor. The rigid drive shaft 128 is rotatably supported within a rigid tubular metal housing 134 by a plurality of spaced apart bearing or spacer blocks 136 (FIGS. 3, 4 and 7). The bearing blocks 136 are disposed at spaced apart locations about the circumference of the drive shaft 128. The bearing blocks 136 are fixedly connected with the stationary housing 134 and support the drive shaft 128 for rotation relative to the housing.

The wires 102 and 104 (FIG. 7) extend through space between adjacent tearing blocks 136. It should be noted that suitable guides (not shown) are provided on the inside of the housing 134 to guide the wires 102 and 104 between the articulated section 34 and the actuator assembly 38. Although many different types of known guides could be used, it is contemplated that it may be preferred to utilize guides having holes through which the wires 102 and 104 extend and which are formed of suitable polymeric material to minimize friction against the surface of the wires 102 and 104.

The wires 102 and 104 are disposed radially outwardly of the rigid metal drive shaft 128 and the flexible drive shaft 130. This allows the outer end portions of the wires 102 and 104 to be fixedly secured to diametrically, opposite portions of the instrument 32 in the manner indicated schematically at 142 and 144 in FIG. 7.

Fluid for irrigating an area adjacent to the cutter 124 is conducted through the conduit 45 formed in the tubular rigid drive shaft 128 and the tubular flexible drive shaft 130 (FIGS. 3, 4 and 5) to the cutter 124. The suction draws the irrigating fluid and any loose tissue away from the cutter 124.

It is contemplated that a thin flexible polymeric sheet my be provided around the articulated section 34. However, the sheet has been omitted in the drawings for purposes of clarity of illustration Second Embodiment In the embodiment of the invention illustrated in FIGS. 1–8, the actuator assembly 38 is operable to bend the articulated section either upwardly or downwardly from the Z axis in the plane of the Y axis (FIG. 8). However, the articulated section 34 is constructed so that it is deflectable or bendable by forces applied to the instrument 32 or the articulated section 34 to deflect the instrument 32 to either side of the plane of the X and Z axes, in the manner indicated schematically in FIG. 8.

Figure 9:
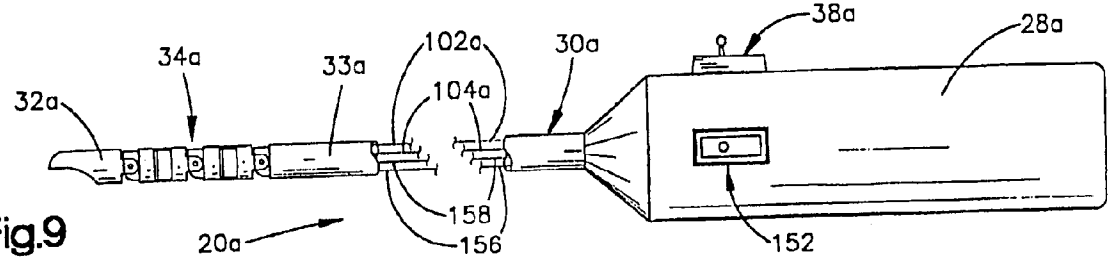
FIG. 9 (on sheet 2 of the drawings) is a fragmentary schematic illustration depicting an embodiment of the invention in which the articulated section can be flexed in any one of four directions by an actuator system.

It is contemplated that it my be desirable to have the actuator assembly 38 constructed in such a manner as to be operable to bend the articulated section 34 in any desired direction. An embodiment of the invention having an actuator assembly constructed so as to deflect the articulated section 34 in my desired direction is illustrated in FIG. 9. Since the embodiment of the invention illustrated in FIG. 9 is generally similar to the embodiment of the invention illustrated in FIGS. 1–8, similar numerals will be utilized to designate similar components, the suffix letter "a" being associated with the numerals of FIG. 9 in order to avoid confusion.

In the embodiment of the invention illustrated in FIG. 9, a surgical instrument 20a has a handle 28a which is connected with an instrument 32a by a stem section 30a. The stem section 30a includes a rigid section 33a and an articulated section 34a.

In accordance with a feature of this embodiment of the invention, an actuator 38a is provided to move the instrument 32a in a plane containing the Z and Y axes (FIG. 8). A second actuator assembly 152 is provided to move the instrument 32a in the plane containing the X and Z axes (FIG. 8). Thus, the two actuator assemblies 38a and 152 function as an actuator system which enables a surgeon to move that instrument 32a anywhere within a hemisphere by operating the actuator assemblies.

The actuator assembly 38a is connected with the instrument 32a by wires 102a and 104a. The actuator assembly 152 is connected with the instrument 32a by wires 156 and 158. The wires 102a, 104a, 156 and 158 are connected with the instrument 32a at locations which are offset from each by 90° about the circumference of the instrument 32a. The wires 102a and 104a are connected with the instrument 32a at locations which are diametrically opposite from each other. The wires 156 and 158 are connected with the instrument 32a at locations which are located diametrically opposite from each other and on a diameter which extends perpendicular to a diameter extending through the connections of the wires 102a and 104a to the instrument 32a. The combination of the four wires 102a, 104a, 156 and 158 and the actuator assemblies 38a and 152 enable the instrument 32a to be pivoted in my desired direction relative to the rigid stem 33a.

In the embodiment of the invention illustrated in FIG. 9, the actuator assembly 152 has the same construction as the actuator assembly 38a. However, it is contemplated that it my be desirable to combine the functions of the actuator assemblies 152 and 38a into a single actuator assembly which would operate all four wires 102a, 104a, 156 and 158. However, it should be understood that the two actuator assemblies 39a and 152 cooperate and function together in such a manner so as to enable a surgeon to move the instrument 32a in my desired direction from the initial position shown in FIG. 9.

Conclusion

The present invention relates to a surgical instrument 20 which is particularly well adapted for arthroscopic and/or endoscopic surgery. The surgical instrument 20 has a stem section 30 which is attached to a handle 28. A suitable instrument 32, such as a cutting tool, is connected with an outer end portion of the stem section 30 by an articulated section 34. An actuator 38 is provided to bend the articulated section 34, to change the orientation of the instrument 32 relative to the stem section 30 and body tissue.

In one embodiment of the invention, a pair of flexible elongated elements 102 and 104, such as wires, are provided to bend the articulated section 23 in opposite directions from an initial position. In this embodiment of the invention, the articulated section 34 may be constructed so as to freely flex in a direction transverse to the direction in which the articulated section is bent by the elongated elements 102 and 104. In another embodiment of the invention (FIG. 9), a plurality of elongated elements 102a, 104a, 156 and 158, such as wires, are provided to flex or bend the articulated section 34a in any one of four directions.

Having described the invention, the following is claimed:

1. A surgical instrument comprising a stem section extending from a handle, a cutting tool, said cutting tool including a rotatable cutter a hollow articulated section connected with said cutting tool and said stem section, a rotatable drive shaft connected with said cutter and disposed in and extending axially through said stem section and said articulated section, said drive shaft having a flexible portion disposed in said articulated section, and actuator means connected with said handle for bending said articulated section and said flexible portion of said drive shaft to change the orientation of said cutter relative to time from a first orientation to a second orientation, said actuator means including first and second elongated elements which extend through said stem section and articulated section and are connected with said cutting tool, said elongated elements being disposed between an outer side surface of said flexible portion of said drive shaft and an inner side of said articulated section, said actuator means including means for pulling on one of said elongated dements to bend said articulated section and said flexible portion or said drive shaft to change the orientation of said cutter from the first orientation to the second orientation, said drive shaft being rotatable relative to said articulated section to rotate said cutter when said cutter is in the first orientation and when said cutter is in the second orientation;

said surgical instrument further including passage means extending axially through said drive shaft for conducting tissue from a location adjacent to said cutter through said articulated section and said stem section toward the handle.

2. A surgical instrument comprising a stem section extending from a handle, a cutting tool, said cutting tool including a rotatable cutter, a hollow articulated station connected with said cutting tool and said stem section, a rotatable drive shaft connected with said cutter and disposed in and extending axially through said stem section and said articulated section, said drive shaft having a flexible portion disposed in said articulated section, and actuator means connected with said handle for bending said articulated section and said flexible portion of said drive shaft to change the orientation or said cutter relative to time from a first orientation to a second orientation, said actuator means including first and second elongated elements which extend through said stem section and articulated section and are connected with said cutting tool, said elongated elements being disposed between an outer side surface of said flexible portion of said drive shaft and in inner side of said articulated section, said actuator means including means for pulling on one of said elongated elements to bend said articulated section and said flexible portion of said drive shaft to change the orientation of said cutter from the first orientation to the second orientation, said drive shaft being rotatable relative to said articulated section to rotate said cutter when said cutter is in the first orientation and when said cutter is in the second orientation;

said surgical instrument further including passage means extending through said drive shaft for conducting irrigating fluid through said drive shaft from said handle to said cutter.

3. A surgical instrument comprising a hollow rigid stem section extending from a handle, a cutting tool, said cutting tool including a rotatable cutter, a hollow articulated section connected with said cutting tool and said stem section, a rotatable drive shaft connected with said cutter and disposed in and extending axially through said stem section and said articulated section, said drive shaft including a rigid section disposed in said stem section and a flexible section disposed in said articulated section, and actuator means connected with said handle for bending said articulated section and said flexible section of said drive shaft to change, the orientation of said cutter relative to tissue from a first orientation to a second orientation, said drive shaft being rotatable relative to said articulated section when said cutter is in the first orientation and when said cutter is in the second orientation, *said actuator means extending through substantially the entire length of said articulated section, said cutting tool being prevented from moving in an axial direction relative to said articulated section*;

said surgical instrument further including passage means extending axially through said drive shaft for conducting tissue from a location adjacent to said cutter through said articulated section and said stem section toward the handle.

4. A surgical instrument comprising a hollow rigid stem section extending from a handle, a cutting tool, said cutting tool including a rotatable cutter a hollow articulated section connected with said cutting tool and said stem section, a rotatable drive shaft connected with said cutter and disposed in and extending axially through said stem section and said articulated section, said drive shaft including a rigid section disposed in said stem section and a flexible section disposed in said articulated section and actuator means connected with said handle for bending said articulated section and said flexible section of said drive shaft to change the orientation of said cutter relative to tissue from a first orientation to a second orientation, said drive shaft being rotatable relative to said articulated section when said cutter is in the first orientation and when said cutter is in the second orientation;

wherein said actuator means includes first and second elongated elements which extend through said stem section and articulated section and are connected with said cutting tool, said elongated elements being disposed between an outer side surface of said flexible section of said drive shaft and an inner side of said articulated section, said actuator means including means for pulling on said first elongated element to bend said articulated section and the flexible section of the drive shaft in a first direction, said actuator means including means for pulling on said second elongated element to bend said articulated section and said flexible section of said drive shaft in a second direction opposite to said first direction.

5. A surgical instrument comprising a hollow rigid stem section extending from a handle, a cutting tool, said cutting tool including a rotatable cutter, a hollow articulated section connected with said cutting tool and said stem section, a rotatable drive shaft connected with said cuter and disposed in and extending axially through said stem section and said articulated section, said drive shaft including a rigid section disposed in said stem section and a flexible section disposed in said articulated section, and actuator means connected with said handle for bending said articulated section and said flexible section of said drive shaft to change the orientation of said cutter relative to tissue from a first orientation to a second orientation, said drive shaft being rotatable relative to said articulated section when said cutter is in the first orientation and when said cutter is in the second orientation, *said actuator means extending through substantially the entire length of said articulated section, said cutting tool being prevented from moving in an axial direction relative to said articulated section*;

said surgical instrument further including passage means extending axially through said drive shaft for conducting irrigating fluid from said handle to said cutter.

6. A surgical instrument comprising a stem section extending from a handle, a movable member, a hollow articulated section connected with said movable member and said stem section, a drive shaft connected with said movable member and disposed in and extending axially through said stem section and said articulated section, said drive shaft having a flexible portion disposed in said articulated section and actuator means a connected with said handle for bending said articulated section and said flexible portion of said drive shaft to change the orientation of said movable member relative to tissue from a first orientation to a second orientation, said actuator means including first and second elongated element which extend through said stem section and *substantially the entire length of* said articulated section and are connected *directly* with said movable member, said actuator means including means for pulling on one of said elongated elements to bend said articulated section and said flexible portion of said drive shaft to change the orientation of said movable member from the first orientation to the second orientation, said drive shaft being movable relative to said articulated section to move said movable member when said movable member is in the first orientation and when said movable member is in the second orientation;

said surgical instrument further including passage means extending axially through said drive shaft for conducting tissue from a location adjacent to said movable member through said articulated section and said stem section toward the handle.

7. A surgical instrument comprising a stem section extending from a handle, a movable member, a hollow articulated section connected with said movable member and said stem section, a drive shaft connected with said movable member and disposed in and extending axially through said stem section and said articulated section, said drive shaft having a flexible portion disposed in said articulated section, and actuator means connected with said handle for bending said articulated section and said flexible portion of said drive shaft to change the orientation of said movable member relative to tissue from a first orientation to a second orientation, said actuator moms including first and second elongated elements which extend through said stem section and *substantially the entire length of* said articulated section and are connected *directly* with said movable member, said actuator means including means for pulling on one of said elongated elements to bend said articulated section and said flexible portion of said drive shaft to change the orientation of said movable member from the first orientation to the second orientation, said drive shaft being movable relative to said articulated section to move said movable member when said movable member is in the first orientation and when said movable member is in the second orientation;

said surgical instrument further including passage means extending through said drive shaft for conducting irrigating fluid through said drive shaft from said handle to said movable member.

[8. A surgical instrument comprising a handle, a stem section extending from add handle, means for acting on tissue including a movable member, a hollow articulated section connected with said movable member and said stem section, means connected with said movable member for moving said movable member relative to said articulated section, said mesas being disposed in and extending axially through said stem section and said articulated section, said means having a flexible portion disposed in said articulated section, said actuator means connected with said handle for bending said articulated section and said flexible portion of acid means for moving said movable member to change the orientation of said movable member relative to tissue from a first orientation to a second orientation, said actuator means including a least one elongate element which extends through said stem section and articulated section and is connected with said movable member, said means for moving said movable member being movable relative to said articulated section to move said movable member relative to said articulated section when said movable member is in the first orientation and when said movable member is in the second orientation;

said surgical instrument further including passage means extending axially through said means for moving said movable member for conducting tissue from a location adjacent to said movable member through said articulated section and said stem section toward said handle.]

[9. A surgical instrument comprising a handle, a stem section extending from said handle, means for acting on tissue including a movable member, a hollow articulated section connected with said movable member and said stem section, means connected with said movable member for moving said movable member relative to said articulated section, odd means being disposed in and extending axially through said stem section and said articulated section, said means having a flexible portion disposed in said articulated section, and actuator means connected with said handle for bending said articulated section and add flexible portion of said means for moving said movable member to change the orientation of said movable member relative to tissue from a first orientation to a second orientation, said actuator means including a least one elongate element which extends through said stem section and articulated section and is connected with said movable member, said means for moving said movable member being movable relative to said articulated section to move said movable member relative to said articulated section when said movable member is in the first orientation and when said movable member is in the second orientation;

said surgical instrument further including passage means extending through said means for moving said movable member for conducting irrigating fluid from said handle to said movable member.]

*10. A surgical instrument comprising:*

*a handle;*

*a stem section extending from said handle;*

*means for acting on tissue including a movable member;*

*a hollow articulated section connected with said movable member and said stem section;*

*means connected to a portion of said movable member for moving said portion relative to said articulated section,*

*said means being disposed in and extending axially through said stem section and said articulated section, said means having a flexible portion disposed in said articulated section; and*

*actuator means connected to said handle for bending said articulated section and said flexible portion of said means for moving said portion of said movable member to change the orientation of said movable member relative to tissue from a first orientation to a second orientation, said actuator means including at least one elongated element which extends through said stem section and substantially the entire length of said articulated section and is connected directly to said movable member;*

*said means for moving said portion of said movable member being movable relative to said articulated section when said movable member is in the first orientation and when said movable member is in the second orientation;*

*said surgical instrument further including passage means for conducting tissue from a location adjacent to said movable member to said handle, said passage means extending axially from said movable member through said articulated section and said stem section to said handle, said passage means extending through said means for moving said portion of said movable member.*

*11. A surgical instrument comprising:*

*a handle;*

*a stem section extending from said handle;*

*means for acting on tissue including a movable member;*

*a hollow articulated section connected to said movable member and said stem section;*

*means connected to a portion of said movable member for moving said portion relative to said articulated section, said means being disposed in and extending axially through said stem section and said articulated section, said means having a flexible portion disposed in said articulated section; and*

*actuator means connected to said handle for bending said articulated section and said flexible portion of said means for moving said portion of said movable member to change the orientation of said movable member relative to tissue from a first orientation to a second orientation, said actuator means including at least one elongated element which extends through said stem section and substantially the entire length of said articulated section and is connected directly to said movable member;*

*said means for moving said portion of said movable member being movable relative to said articulated section to move said movable member relative to said articulated section when said movable member is in the first orientation and when said movable member is in the second orientation;*

*said surgical instrument further including passage means for conducting irrigating fluid from said handle to said movable member, said passage means extending axially from said handle through said articulated section and said stem section to said movable member, said passage means extending through said means for moving said portion of said movable member.*

* * * * *

UNITED STATES PATENT AND TRADEMARK OFFICE

CERTIFICATE OF CORRECTION

PATENT NO. : RE 39,152 E
APPLICATION NO. : 09/707445
DATED : June 27, 2006
INVENTOR(S) : Gilbert M. Aust It is certified that error appears in the above-identified patent and that said Letters Patent is hereby corrected as shown below:

Column 9, line 33, before “from ”delete “time” and insert --tissue--.
Column 9, line 41, after “elongated” delete “dements” and insert --elements--.
Column 9, line 42, after “portion” delete “or” and insert --of--.
Column 9, line 55, after “articulated” delete “station” and insert --section--.
Column 9, line 63, before “from” delete “time” and insert --tissue--.
Column 11, line 5, after “said” delete “cuter” and insert --cutter--.
Column 11, line 30, after “means” delete “a”.

Signed and Sealed this

Third Day of April, 2007

JON W. DUDAS
*Director of the United States Patent and Trademark Office*